United States Patent [19]

Patchett et al.

[11] Patent Number: 4,555,502

[45] Date of Patent: Nov. 26, 1985

[54] AMINOACYL-CONTAINING DIPEPTIDE DERIVATIVES USEFUL AS ANTIHYPERTENSIVES

[75] Inventors: Arthur A. Patchett, Westfield; Mu T. Wu, Clark, both of N.J.

[73] Assignee: Merck & Co., Inc., Rahway, N.J.

[21] Appl. No.: 425,133

[22] Filed: Sep. 30, 1982

[51] Int. Cl.$^4$ .................. A61K 37/00; C07C 103/52; C07D 209/20; C07D 209/18
[52] U.S. Cl. .............................. 514/19; 260/112.5 R; 548/492
[58] Field of Search ................ 260/239.3 T, 112.5 R; 548/492; 424/177; 514/19

[56] References Cited

U.S. PATENT DOCUMENTS

| | | | |
|---|---|---|---|
| 4,303,583 | 12/1981 | Kim et al. | 260/239.3 T |
| 4,374,829 | 2/1983 | Harris et al. | 424/177 |
| 4,385,180 | 5/1983 | Kim et al. | 548/492 |

FOREIGN PATENT DOCUMENTS

| | | | |
|---|---|---|---|
| 2095252 | 9/1982 | United Kingdom | 260/112.5 R |
| 2095682 | 10/1982 | United Kingdom | 260/112.5 R |

*Primary Examiner*—Delbert R. Phillips
*Attorney, Agent, or Firm*—Salvatore C. Mitri; Michael C. Sudol

[57] ABSTRACT

The invention relates to aminoacyl-containing dipeptide derivatives and related compounds which are useful angiotensin converting enzyme inhibitors and as antihypertensives.

21 Claims, No Drawings

AMINOACYL-CONTAINING DIPEPTIDE DERIVATIVES USEFUL AS ANTIHYPERTENSIVES

BACKGROUND OF INVENTION

The invention in its broad aspects relates to aminoacyl-containing dipeptide derivatives and related compounds which are useful as converting enzyme inhibitors and as antihypertensives. The compounds of this invention are represented by the following formula:

$$\begin{array}{c} R_3 \\ | \\ COC-(CH_2)_r-NHR_5 \\ | \quad | \\ \quad R_4 \\ N-R_2 \\ | \\ (CH_2)_n \quad A \quad B \\ | \qquad | \quad | \\ R_1-CH-NH-CH-CON-CH \\ | \qquad\qquad\qquad | \\ CO_2R \qquad\qquad\qquad CO_2R_7 \end{array} \quad I$$

wherein

R and $R_7$ are independently hydrogen, loweralkyl, aryl, aralkyl;

$R^1$ is hydrogen; alkyl of from 1–12 carbon atoms which include branched and unsaturated groups and cyclic groups of 3–9 carbon atoms; substituted lower alkyl of 2–8 carbon atoms wherein the substituent(s) are halo, hydroxy, carboxy, carboxamido, loweralkylthio, loweralkoxy, loweralkoxycarbonyl, arylthio, aryloxy, aralkylthio, aralkyloxy, amino, loweralkylamino, diloweralkylamino, arylamino, arloweralkylamino, acylamino, acyl loweralkylamino, acyl arylamino, acyl aralkylamino, =O, =S or ureido; benzofused cycloalkyl and bicycloalkyl of 8 to 12 carbon atoms which can be substituted by one or more of the foregoing substituents; aryl, arloweralkyl, heteroaryl, heteroarloweralkyl, and those groups substituted by one or more of the foregoing substituents, the aryl or heteroaryl portions thereof being optionally mono-, di- or trisubstituted by halo, loweralkyl, hydroxy, loweralkoxy, amino, aminoloweralkyl, substituted aminoloweralkyl, hydroxyloweralkyl, acylamino, carboxy, halolower alkyl, nitro, cyano or sulfonamido; all of said foregoing substituents containing an aryl or heteroaryl group in which the aromatic rings are partially or completely hydrogenated;

n is 1 to 5;
r is 0 to 3;
$R_2$ is hydrogen, loweralkyl;
$R_3$ is hydrogen, aryl, hydroxyaryl, loweralkyl, loweralkyl substituted with aryl, carboxy, heteroaryl, amino, hydroxy, guanidino, alkylthio, mercapto, or alkyloxy;
$R_4$ and $R_5$ are independently hydrogen, loweralkyl; or,
$R_3$ and $R_5$ can be joined to form a 5- to 6-membered ring having the formula:

$$H-N\diagup\!\!\!\diagdown_V$$

wherein V is $-CH_2CH_2-$, $-CH_2-$, S, $-CH(OR_2)-$ and wherein $R_2$ is the same as defined above;

A is loweralkyl, $C_3-C_8$ cycloalkyl; $C_8-C_{12}$ bicycloalkyl; benzofused $C_3-C_8$ cycloalkyl; perhydrobenzofused $C_3-C_8$ cycloalkyl; aryl; aralkyl; heteroaryl; heteroaralkyl; perhydroheteroaryl, or perhydroheteroaralkyl; all of which can be substituted by loweralkyl, loweralkoxy, halo, hydroxy, amino or acylamino;

B is hydrogen or loweralkyl; or, A and B can be joined, together with the N and C atoms to which they are attached to form a ring having the formulae $$\begin{array}{c} X-Y \\ N\diagup \quad \diagdown \\ \quad\diagdown_{(CH_2)_p} \\ ROOC \quad COOR \quad Z \end{array} \qquad -N\diagup\diagdown\!\!\diagup\!\!R_8$$

$$-N\diagup\diagdown\!\!\diagup\!\!R_8 (\quad)_q$$
$$COOR \quad Z$$

wherein:
X and Y taken together are $-CH_2-CH_2-$, $$\underset{R_6}{CH-S-},\ \underset{O\ R_9}{-\overset{O}{\overset{\|}{C}}-\overset{}{\underset{}{CH}}-},\ \underset{R_6}{CH-\overset{O}{\overset{\|}{C}}-},\ -\overset{O}{\overset{\|}{C}}-O,$$

$$-\overset{O}{\overset{\|}{C}}-S-CH_2-\underset{R_6}{\overset{R_9}{\overset{|}{CH}}},\ \underset{R_6}{\overset{R_9}{\overset{|}{CH}}}-CH_2 -\overset{O}{\overset{\|}{C}}-\underset{}{\overset{R_{10}}{\overset{|}{N}}},\ or\ -CH_2-\underset{R_{10}}{\overset{R_9}{\overset{|}{C}}}-$$

wherein $R_6$ is hydrogen or loweralkyl;

$R_9$ is hydrogen; lower alkyl; cycloalkyl; aryl; aralkyl; heteroaryl; heteroaralkyl; loweralkyloxy; loweralkylthio; aryloxy; arylthio; arloweralkyloxy; arloweralkylthio; acyloxy; amino; mono- or disubstituted loweralkylamino and arloweralkylamino; heteroarloweralkylamino; acylamino in which the acyl group can be loweralkanoyl, arloweralkanoyl, aroyl, heteroaroyl, heteroarloweralkanoyl; carbamoyloxy; or, N-substituted carbamoyloxy; the aromatic ring in said foregoing substituents being optionally mono-, di- or trisubstituted by loweralkyl, loweralkoxy, hydroxy, amino, loweralkylthio, halo, lowerhydroxyalkyl, loweraminoalkyl, sulfonamido, cyano, nitro, aryl, aryloxy, arylthio, or aralkyl; the aromatic rings in said groups containing aryl or heteroaryl groups being completely or partially hydrogenated;

$R_{10}$ is hydrogen; loweralkyl; aryl; substituted aryl; aralkyl; or, cycloalkyl; or $R_9$ and $R_{10}$ taken together can form a 5 or 6 membered ring which can contain 0, 1 or 2 S or O atoms;

p is 1 to 3;
q is 1 to 3;
W is absent; $-CH_2$, or $$-\overset{O}{\overset{\|}{C}}-;$$

Z is —(CH$_2$)$_m$— wherein m is 0 to 2 provided that m is not O when W is absent;

R$_8$ is hydrogen; loweralkyl; loweralkoxy; hydroxy, halo; loweralkylthio; or, amino; and, the pharmaceutically acceptable salts thereof.

Except where otherwise indicated: the loweralkyl substituents recited above denote straight, branched, saturated or unsaturated hydrocarbon radicals of from one to six carbon atoms such as, for example, methyl, ethyl, n-propyl, i-propyl, n-butyl, i-butyl, t-butyl, n-pentyl, i-pentyl, n-hexyl, vinyl, propargyl, allyl, butenyl, and the like;

loweralkoxy and aryloxy substituents denote loweralkyl and aryl groups attached through an oxygen bridge;

arloweralkyl substituents denote phenyl, naphthyl, or biphenyl attached through a straight or branched chain hydrocarbon of from one to six carbon atoms such as, for example, benzyl;

bicycloalkyl denotes two 5-7 membered cycloalkyl rings fused together such as, for example, perhydroindane, perhydronaphthalene, and the like;

halo denotes chloro, bromo, iodo, or fluoro;

aryl denotes phenyl, naphthyl, or biphenyl;

heteroaryl substituents denote 5- or 6-membered aromatic ring or rings containing 1-3 heteroatoms selected from N, O, and S such as, for example, pyridyl, thienyl, furyl, imidazolyl, thiazolyl, and the like, as well as bicyclic groups in which any of the foregoing heterocyclic rings is fused to another aromatic ring such as, for example, indolyl, quinolinyl, isoquinolinyl, benzimidazolyl, benzothiazolyl, benzothienyl, naphthyridyl, and the like;

substituted aryl denotes aryl rings substituted with hydroxy, loweralkoxy, or halo;

substituted heteroaryl denotes such ring groups substituted with hydroxy, amino, loweralkoxy, or halo;

partially or completely hydrogenated aryl or heteroaryl denote such ring groups in which one or more of the double bonds has (have) been reduced such as, for example, indolinyl, tetralyl, tetrahydroisoquinolyl, piperidinyl, and the like;

acylamino denotes loweralkanoylamino (such as acetylamino), aroylamino (such as benzoylamino), heteroaroylamino (such as thienoylamino), aralkanoylamino (such as phenylbutanoylamino), substituted alkanoylamino and substituted aralkanoylamino in which the substituents are hydroxy, oxo, or amino (such as carbobenzyloxyamino, phenylalanylamino, glycylamino, serylamino, β-alanylamino, and the like).

Preferred are those compounds of Formula I wherein:

R and R$_7$ are independently hydrogen; loweralkyl; aralkyl;

R$_1$ is as defined above;

n is 2 to 5;

r is 0;

R$_3$ is hydrogen, aryl, hydroxyaryl, loweralkyl, loweralkyl substituted with aryl, carboxy, heteroaryl, amino, hydroxy, guanidino, or alkylthio groups;

R$_3$ and R$_5$ can be joined to form a 5- to 6-membered ring having the forumla:

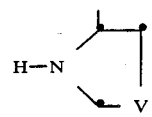

wherein V is —CH$_2$, S, —CH—OR$_2$—;

R$_4$ is hydrogen;

A is cycloalkyl containing 3-8 carbons in the ring, C$_{9-10}$ bicycloalkyl, benzofused cycloalkyl, or perhydrobenzofused cycloalkyl;

B is hydrogen or A and B can be joined together to form a ring in which p is 1;

q is 1-2; and,

X and Y taken together are —CH$_2$CH$_2$—, CHR$_6$S, COCH$_2$, CH$_2$CHR$_9$, CH$_2$CO, CH$_2$CHOR$_9$, wherein R$_6$ is hydrogen and R$_9$ is hydrogen, loweralkyl, aryl, or cycloalkyl, or X and Y taken together with the N and C atoms to which they are attached are joined to form a ring having the formulae:

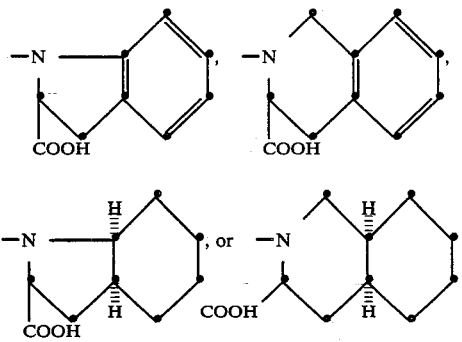

Still more preferred are those compounds of Formula I wherein:

R and R$_7$ are independently hydrogen, loweralkyl, benzyl;

R$_1$ is alkyl having from 1 to 8 carbon atoms; substituted lower alkyl wherein the alkyl group has 1-5 carbon atoms and the substituent is amino, arylamino, acylarylamino, arylthio, aryloxy or arylamino; aralkyl or heteroaralkyl wherein the alkyl portion has 1 to 3 carbon atoms (such as phenethyl or imidazolylethyl) or substituted arloweralkyl and substituted heteroarloweralkyl wherein the alkyl groups have 1-3 carbons and wherein the substituent(s) is (are) halo, nitro, cyano, sulfonamido, amino, aminoalkyl, hydroxyalkyl, hydroxy, lower alkoxy or lower alkyl and on the alkyl group the substituents are optionally amino, acylamino and hydroxy;

n is 2 to 4;

r is 0;

R$_3$ is hydrogen, aryl, hydroxyaryl, loweralkyl, loweralkyl substituted with aryl, carboxy, heteroaryl, amino, hydroxy, guanidino, or alkylthio groups, R$_2$, R$_4$ and R$_5$ are hydrogen;

A is cyclopentyl or indanyl;

B is hydrogen; and, p is 1;

q is 1-2; and,

X and Y taken together are —CH$_2$CH$_2$—, CHR$_6$S, CH$_2$CHR$_9$, COCH$_2$, CH$_2$CHOR$_9$ wherein R$_6$ is hydrogen and R$_9$ is aryl or cycloalkyl; or X and Y taken together with the N and C atoms to which they are attached are joined to form a ring having the formulae:

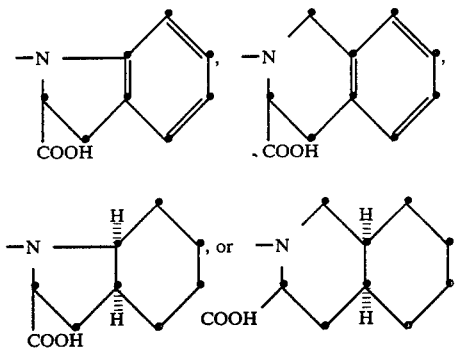

Most preferred are compounds of Formula I wherein:

R and R$_7$ are independently hydrogen, loweralkyl, benzyl;

R$_1$ is alkyl having from 1 to 8 carbon atoms; substituted lower alkyl wherein the alkyl group has 1-5 carbon atoms and the substituent is amino, aroylamino, aroylarylamino, aroylaralkylamino, arylthio or aryloxy; aralkyl or heteroaralkyl wherein the alkyl portion has 1 to 3 carbon atoms (such as phenethyl or imidazolylethyl) or substituted aralkyl and substituted heteroaralkyl wherein the alkyl groups have 1-3 carbons and wherein the substituent(s) is (are) amino, hydroxy, aroylamino or heteroaroylamino and the aryl and heteroaryl substituents are hydroxy, amino, aminomethyl, nitro, cyano, halo, or sulfonamido;

n is 2 to 4;

r is 0;

R$_2$ is hydrogen;

R$_3$ is hydrogen, loweralkyl, loweralkyl substituted with aryl, carboxy, heteroaryl, guanidino, amino, or hydroxy;

R$_3$ and R$_5$ can be joined to form a pyrrolidine ring;

R$_4$ is hydrogen;

A is cyclopentyl or indanyl;

B is hydrogen, or p is 1;

q is 1-2; and,

X and Y taken together are CH$_2$CH$_2$, CH$_2$S, CH$_2$CHOH, CH$_2$CHR$_9$ wherein R$_9$ is cyclohexyl or phenyl, or X and Y taken together with the N and C atoms to which they are joined form a ring having the formulae:

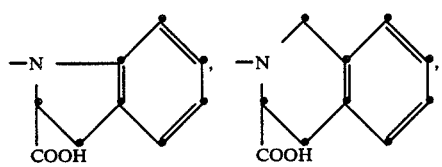

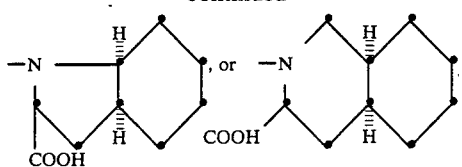

The preferred, more preferred and most preferred compounds also include the pharmaceutically acceptable salts thereof.

The products of Formula (I) can be produced by the methods depicted in the following Reaction Schemes wherein R, R$_1$, R$_2$, R$_3$, R$_4$, R$_5$, R$_6$, R$_7$, R$_8$, r$_9$, n, p, q, r, A, B, U, V, W, X, Y and Z are as defined above. Reactive functionality in these groups is protected as needed with suitable protecting groups as is well known to those skilled in peptide chemistry.

In general, the compounds of this invention can be prepared by reacting a compound having the formula:

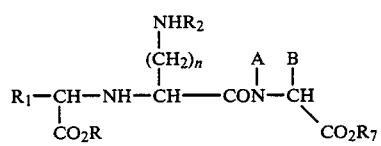

wherein R, R$_1$, R$_2$, R$_7$, A, B and n are as defined above, with a carboxy activated derivative of a compound having the formula:

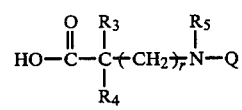

wherein R$_3$ and R$_4$ are as defined above and Q is a suitable protecting group such as t-butoxycarbonyl, benzyloxycarbonyl, and like groups. Activation of the carboxy derivative III is typically accomplished with N-hydroxysuccinimide or N-hydroxybenzotriazole esters. Subsequent removal of the Q protecting group using standard conditions yield compounds of Formula I.

Amino acid derivative III can also be coupled to dipeptide derivative II using dicyclohexylcarbodiimide or diphenylphosphorylazide providing neither R nor R$_7$ are hydrogen. When either R or R$_7$ are hydrogen in products of Formula I, the carboxyls in intermediate compounds II should be protected as removable esters such as, for example, with R and/or R$_7$ benzyl or t-butyl groups.

In the above-described synthesis, only slightly more than one equivalent of activated amino acid derivative III is used to minimize reaction with the NH of intermediate II to which R$_1$CHCO$_2$R is attached. Alternatively, this NH can be protected during this step with a removable group such as, for example, a formyl function.

Additionally, compounds of Formula I can be synthesized in a step-wise manner as illustrated in the following Reaction Schemes.

REACTION SCHEME I

-continued

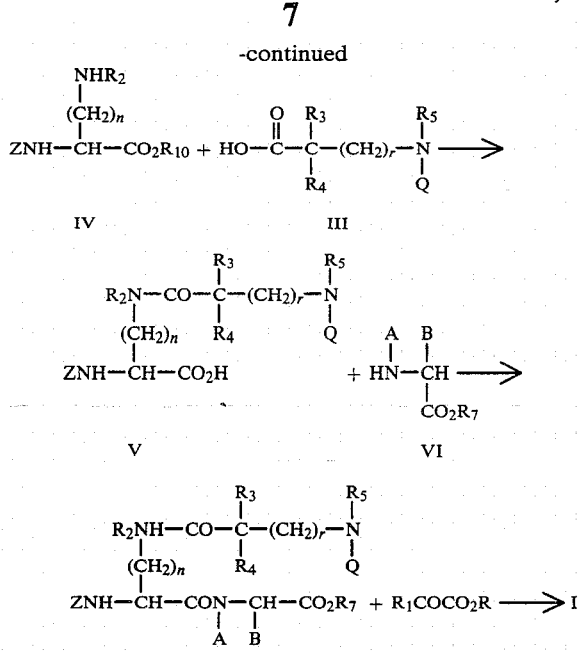

REACTION SCHEME II

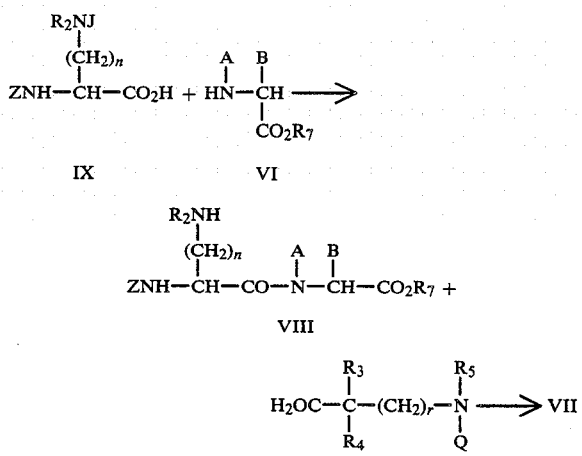

REACTION SCHEME III

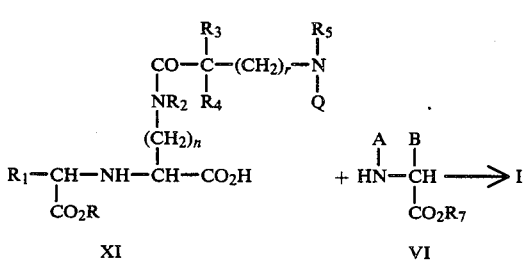

In Reaction Scheme I, Z and Q are suitable removable nitrogen protecting groups such as t-butoxycarbonyl or benzyloxycarbonyl functions and $R_{10}$ is a removable carboxyl protecting group such as benzyl or t-butyl. The addition and removal of these protecting groups is achieved under standard conditions. Similarly, the peptide coupling reactions of intermediates III with IV and V with VI are conducted with coupling reagents standard in peptide chemistry, some of which are noted above while others are illustrated in the Examples set forth hereinbelow.

The reductive coupling of $R_1COCO_2R$ to intermediate VII ($Z=H$) is achieved by the use of sodium cyanoborohydride or with hydrogen in the presence of catalysts such as palladium or Raney nickel.

In Reaction Scheme II, dipeptide VIII results from the coupling of intermediates IX and VI in which protecting group J is subsequently removed in the presence of protecting group Z. Intermediate III is then coupled to intermediate VIII in the same manner as described for the synthesis of V from the coupling of III with IV in Reaction Scheme I.

Reaction Scheme III illustrates a further synthetic variant wherein the order of the coupling reactions is changed so that properly protected XI is coupled to intermediate VI to yield products of Formula I. In this coupling reaction, neither R nor Q is hydrogen, but either may subsequently be converted to hydrogen by standard methods, if this is desired.

Formula I compounds wherein $R_2$=loweralkyl can be prepared by reacting intermediates II, IV and VIII ($R_2$=H) with aldehydes (1 molar equivalent) in the presence of $NaCNBH_3$, or stepwise by first forming the N-benzyl derivative using 1 equivalent of benzaldehyde and $NaCNBH_3$, followed by treatment with formaldehyde or loweralkylaldehyde with $NaCNBH_3$, and finally removing the benzyl protecting groups by hydrogenolysis using Pd/C catalyst.

The above described syntheses can utilize racemates, enantiomers or diastereomers as starting materials or as intermediates. When diastereomeric products result from the synthetic procedures, the diastereomeric products can be separated by conventional chromatographic or fractional crystallization methods.

In products of general Formula I, the carbon atoms to which the group, $(CH_2)_nNR_2COCR_3R_4(CH_2)_rNR_5H$, is attached is asymmetric as are the carbons to which $R_1$, $R_3$, $R_4$ and B are attached when these groups are not hydrogen. In general, L-amino acid configurations are preferred throughout. However, at the carbons to which $R_3$, $R_4$ and B are attached, D-amino acid configurations are sometimes consistent with good activity and confer additional metabolic stability. In most instances, L-amino acid configurations can be alternatively designated as (S)- and D-amino acid configurations as (R)-configurations.

The compounds of this invention form salts with various inorganic and organic acids and bases which are also within the scope of the invention. Such salts include ammonium salts, alkali metal salts like sodium and potassium salts, alkaline earth metal salts like the calcium and magnesium salts, salts with organic bases e.g., dicyclohexylamine salts, N-methyl-D-glucamine, salts with amino acids like arginine, lysine and the like. Also salts with organic and inorganic acids may be prepared, e.g., HCl, HBr, $H_2SO_4$, $H_3PO_4$, methanesulfonic, toluensulfonic, maleic, fumaric, camphorsulfonic acid. The non-toxic physiologically acceptable salts are preferred, although other salts are also useful, e.g., in isolating or purifying the product.

The salts may be formed by conventional means as by reacting the free acid or free base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

The compounds of this invention inhibit angiotensin converting enzyme and thus block conversion of the decapeptide angiotensin I to angiotensin II. Angiotensin II is a potent pressor substance. Thus, blood-pressure lowering can result from inhibition of its biosynthesis especially in animals and humans whose hypertension is angiotensin II related. Furthermore, converting enzyme degrades the vasodepressor substance, bradykinin. Therefore, inhibitors of angiotensin converting enzyme may lower blood-pressure also by potentiation of bradykinin. Although the relative importance of these and other possible mechanisms remains to be established, inhibitors of angiotensin converting enzyme are effective antihypertensive agents in a variety of animal models and are useful clinically, for example, in many human patients with renovascular, malignant and essential hypertension and in the treatment of congestive heart failure. See, for example, D. W. Cushman et al., *Biochemistry* 16, 5484 (1977).

The evaluation of converting enzyme inhibitors is guided by in vitro enzyme inhibition assays. For example, a useful method is that of Y. Piquilloud, A. Reinharz and M. Roth, *Biochem. Biophys. Acta*, 206, 136 (1970) in which the hydrolysis of carbobenzyloxyphenylalanylhistidinylleucine is measured. In vivo evaluations may be made, for example, in normotensive rats challenged with angiotensin I by the technique of J. R. Weeks and J. A. Jones, *Proc. Soc. Exp. Biol. Med.*, 104, 646 (1960) or in a high renin rat model such as that of S. Koletsky et al., *Proc. Soc. Exp. Biol. Med.* 125, 96 (1967).

Thus, the compounds of this invention are useful as antihypertensives in treating hypertensive mammals, including humans, and they can be utilized to achieve the reduction of blood pressure by formulating in compositions such as tablets, capsules or elixirs for oral administration or in sterile solutions or suspensions for parenteral administration. The compounds of this invention can be administered to patients in need of such treatment in a dosage range of 0.5 to 100 mg per patient generally given several times, thus giving a total daily dose of from 0.5 to 400 mg per day. The dose will vary depending on severity of disease, weight of patient and other factors which a person skilled in the art will recognize.

It is often advantageous to administer compounds of this invention in combination with other antihypertensives and/or diuretics. For example, the compounds of this invention can be given in combination with such compounds as amiloride, atenolol, bendroflumethiazide, chlorothalidone, chlorothiazide, clonidine, cryptenamine acetate and cryptenamine tannates, deserpidine, diazoxide, ethacrynic acid, furosemide, guanethidene sulfate, hydralazine hydrochloride, hydrochlorothiazide, hydroflumethiazide, metolazone, metoprolol tartate, methyclothiazide, methyldopa, methyldopate hydrochloride, minoxidil, (S)-1-{[2-(3,4-dimethoxyphenyl)ethyl]amino}-3-{[4-(2-thienyl)-1H-imidazol-2-yl]phenoxy}-2-propanol, polythiazide, the pivaloyloxyethyl ester of methyldopa, indacrinone and variable ratios of its enantiomers, nifedipine, verapamil, diltiazam, flumethiazide, bendroflumethiazide, atenolol, (+)-4-{ 3-}-[2-(1-hydroxy-cyclohexyl)ethyl]-4-oxo-2-thiazolidinyl}propyl}benzoic acid, bumetanide, prazosin, propranolol, rauwolfia serpentina, rescinnamine, reserpine, spironolactone, timolol, trichlormethiazide, benzthiazide, quinethazone, tricrynafan, triamterene, acetazolamide, aminophylline, cyclothiazide, merethoxylline procaine, and the like, as well as admixtures and combinations thereof.

Typically, the individual daily dosages for these combinations can range from about one-fifth of the minimally recommended clinical dosages to the maximum recommended levels for the entities when they are given singly.

To illustrate these combinations, one of the antihypertensives of this invention effective clinically in the 2.5–100 milligrams per day range can be effectively combined at levels at the 0.5–100 milligrams per day range with the following comounds at the indicated per day dose range: hydrochlorothiazide (10–100 mg), timolol (5–60) mg), methyl dopa (65–2000 mg), the pivaloyloxyethyl ester of methyl dopa (30–1000 mg), indacrinone and variable ratios of its enantiomers (25–150 mg) and (+)-4- {3-{[2-(1-hydroxycyclohexyl)ethyl]-4-oxo-2-thiazolidinyl}propyl}-benzoic acid (10–100 mg).

In addition, the triple drug combinations of hydrochlorothiazide (10–100 mg) plus timolol (5–60 mg) plus converting enzyme inhibitor of this invention (0.5–100 mg) or hydrochlorothiazide (10–100 mg) plus amiloride (5–20 mg) plus converting enzyme inhibitor of this invention (0.5–100 mg) are effective combinations to control blood pressure in hypertensive patients. Naturally, these dose ranges can be adjusted on a unit basis as necessary to permit divided daily dosage and, as noted above, the dose will vary depending on the nature and severity of the disease, weight of patient, special diets and other factors.

Typically, the combinations shown above are formulated into pharmaceutical compositions as discussed below.

About 0.5 to 100 mg of a compound or mixture of compounds of Formula I or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which may be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule, it may contain, in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc. or a synthetic fatty vehicle like ethyl oleate or the like. Buffers, preservatives, antioxidants and the like can be incorporated as required.

The following examples are illustrative of the invention and constitute especially preferred embodiments. The preferred diastereomers of these examples are isolated by conventional column chromatography or fractional crystallization.

EXAMPLE 1

N-[$N^2$-(1-Carboxy-3-phenylpropyl)-$N^4$-glycyl-L-2,4-diamino-N-butyryl]-L-proline $N^4$-(Benzyloxycarbonyl)-L-2,4-diamino-N-butyric acid was prepared from L-2,4-diamino-N-butyric acid and N-benzyloxycarbonyloxy-5-norborene-2,3-dicarboximide by the method of A. Paquet (*Can. J. Chem.*, 54, 733, 1976). The $N^2$-amino group was protected with tert-butoxycarbonyl using di-tert-butyl dicarbonate. The resulting, fully protected L-2,4-diamino-n-butyric acid was condensed with L-proline-tert-butyl ester in the presence of N,$N^1$-dicyclohexylcarbodiimide. Via hydrogenation (10% Pd/c, RT, 40 psi) the benzyloxycarbonyl was removed from $N^4$, then the free amine was coupled with N-benzyloxycarbonyl glycine using N,N'-dicyclohexylcarbodiimide. Purification of the fully protected intermediate was effected on silica gel (LPS-2, low pressure LC, EtOAc). Treatment of N-[$N^2$-tert, butyoxycarbonyl-$N^4$-(N-benzyloxycarbonyl glycyl]-L-2,4-diamino-N-butyryl]-L-proline-tert-butyl ester with trifluoroacetic acid for one hour at room temperature removed the tert-butoxycarbonyl and tert-butyl ester protecting groups. The resulting trifluoroacetate salt (1.12 g, 2.16 mmol) and 2-oxo-4-phenyl-butyric acid (1.92, 10.8 mmol) were dissolved in methanol/water (1:1) and adjusted to pH 7 with sodium hydroxide. A solution of sodium cyanoborohydride (407 mg, 6.48 mmol) in methanol was added at the rate of 1 ml/hr by syringe pump. When the reaction was completed, the product was absorbed on Dowex 50 ($H^+$), (50–100 mesh). The ion exchange column was rinsed to neutrality with water, then eluted with 2% pyridine in water followed by LH-20 ($CH_3OH$) chromatography. Product-rich fractions were evaporated to dryness then freeze-dried to a white fluffy solid (900 mg).

Removal of the benzyloxycarbonyl group was accomplished by treatment with 30–32% HBr in glacial acetic acid (7 ml) for 15 minutes at room temperature. The resulting HBr salt was absorbed on Dowex 50 ($H^+$). The free amine was eluted from the column with 2% pyridine in water. Evaporation, then freeze-drying of product fractions afforded N-[$N^2$-(1-carboxy-3-phenylpropyl)-$N^4$-glycyl-L-2,4-diamino-N-butyryl]-L-proline as a white fluffy solid (355 mg). The spectral data were consistent with structure.

EXAMPLE 2

N-[$N^2$-(1(S)-Carboxy-3-phenylpropyl)-$N^6$-glycyl-L-lysyl]-L-proline

A solution of 405 mg (1.0 mmol) of N-[$N^2$-(1(S)-carboxy-3-phenylpropyl)-L-lysyl]-L-proline and 252 gm (3.0 mmol) of sodium bicarbonate in 3 ml of water was treated with a solution of 272 mg (1.0 mmol) of N-t-butoxycarbonyl-glycine N-hydroxysuccinimide ester in 2 ml acetonitrile. The resulting clear solution was stirred at room temperature for 1½ hours, concentrated in vacuo to ¾ volume and acidified by dropwise addition of 2.5 N HCl. The resulting mixture was shaken with a small amount of ethyl acetate and the ethyl acetate/water layer decanted off a white, insoluble gum. The insoluble gum was flushed in vacuo with methanol and pumped out on an oil pump to provide 395 mg of crude product contaminated with a small amount of starting material. LH-20 Chromatograph (2.5×240 cm, methanol system) yield 305.6 mg of N-[$N^2$-(1(S)-carboxy-3-phenylpropyl)-$N^6$-(N-tert-butoxycarbonylglycyl)-L-lysyl]-L-proline. 305 mg (0.54 mmol) of the above intermediate was then dissolved in 8 ml trifluoroacetic acid (drying tube) and stirred at room temperature for 20 minutes. The reaction mixture was concentrated in vacuo, flushed 2x with ethyl ether and pumped out on an oil pump. The residual dry, white foam was dissolved in 8 ml of water and put on a column of 8 ml of Dowex 50W-X2($H^+$) resin. After aqueous washes, the product was eluted with water containing 2% pyridine, which after freeze-drying, provided 265 mg of N-[$N^2$-(1(S)-carboxy-3-phenylpropyl)-$N^6$-glycyl-L-lysyl]-L-proline that was single spot by tlc (ethyl acetate/pryridine/acetic acid/water (10:5:1:3) system) and had an excellent nmr in deuteromethanol (aromatic singlet at 7.2 ppm and the glycyl methylene at 3.7 ppm).

EXAMPLE 3

N-[$N^2$-(-Carboxy-3-phenylpropyl)-$N^3$-L-alanyl-L-2,3-diaminopropyl]-L-proline $N^3$-(Benzyloxycarbonyl)-L-2,3-diaminopropionicacid was prepared as described in the literature (M. Goodman, *J. Med. Chem.*, 23, 417, 1980). The $N^2$-amino group was blocked with tert-butoxycarbonyl using di-tert butyl dicarbonate in the usual manner. The resulting N-protected amino acid (2.63 g, 7.77 mmol) was coupled with L-proline-tert-butyl ester (1.46 g, 8.55 mmol) using DCC (1.76 g, 8.55 mmol). Following hydrogenation (10% Pd-c) the $N^3$-group (2.12 g) was coupled with N-benzyloxycarbonyl-L-alanine to afford fully protected intermediate, $N^2$-tert-butoxycarbonyl-$N^3$-(N-benzyloxycarbonyl-L-alanyl)-L-2,3-diaminopropyl-L-proline-tert-butyl ester (1.6 g). Low pressure liquid chromatography (LPS-2), EtOAc gave good purity material. Treatment with TFA deblocked the $N^2$-position and tert-butyl ester (84% yield). The TFA salt was reductively alkylated in the established manner (5 mol eqs 2-oxo-4-phenylbutyric acid, 3 mol eqs $NaCNBH_3$, $CH_3OH$-$H_2O$, 1:1) (74% yield). Subsequent removal of benzyloxycarbonyl group with 30–32% HBr/HOAc gave the desired product as a salt which was liberated on Dowex 50($H^+$) and further purified on an LH-20 column to give N-[$N^2$-(1-carboxy-3-phenylpropyl)-$N^3$-L-alanyl-L-2,3-diaminopropyl]-L-proline, in 60% yield. Both mass spectra and nmr were consistent with the desired structure.

EXAMPLE 4

N-[$N^2$-(1-Carboxy-3-phenylpropyl)-$N^5$-glycyl-L-ornithyl]-L-proline

The coupling of $N^2$-t-Boc-$N^5$-Cbz-L-ornithine (7.5 g, 20.5 mmol) and L-proline-t-butyl ester (3.85 g, 22.5 mmol) using standard DCC conditions (4.64 g, 22.5 mmol) afforded $N^2$-t-Boc-$N^5$-Cbz-L-ornithyl-L-proline-t-butyl ester in quantitative yield. A described in Example 1, Cbz was removed via hydrogenation, and the amine was coupled to N-Cbz-glycine. Following low pressure HPLC (LPS-2 $SiO_2$, EtOAc), the pure tripeptide was treated with TFA then reductively alkylated with 2-oxo-4-phenylbutyric acid/NaCNBH₃ in the established manner. Work up on Dowex 50(H+) then purification on LH-20 gave pure desired product with the Cbz in the glycyl nitrogen. Cleavage of the Cbz with 30-32% HBr/HOAc followed by Dowex treatment to free the amine yielded high purity N-[N²-(1-carboxy-3-phenylpropyl)-N⁵-glycyl-L-ornithyl]-L-proline. All data (ms, nmr and tlc) were consistent with the structure.

EXAMPLE 5

N-[N²-(Ethoxycarbonyl-3-phenylpropyl)-N⁵-glycyl-L-ornithyl]-L-proline

N-[N⁵-(N-Cbz-glycyl)-L-ornithyl]-L-proline was prepared as described in Example 4. The reductive alkylation of TFA salt (132 mg, 0.314 mmol) with ethyl 2-oxo-4-phenylbutyrate (324 mg, 1.57 mmol) and sodium cyanoborohydride (59.2 mg, 0.942 mmol) was carried out in the usual manner. The work up, including 30-32% HBr/HOAc treatment, was the same as that described in Example 1. Both ms and nmr were consistent with the structure for N-[N²-(1-ethoxycarbonyl-3-phenylpropyl)-N⁵-glycyl-L-ornithyl]-L-proline (47.5 mg).

EXAMPLE 6

N-[N²-(1-Carboxy-3-phenylpropyl)-N³-β-alanyl-L-2,3-diaminopropyl]-L-proline

N-[N²-t-Boc-N³-(N-Cbz-β-alanyl)-L-2,3-diaminopropyl]-L-proline-t-butyl ester was prepared in the same manner as that described for preparing N-[N²-t-Boc-N³-(N-Cbz-L-alanyl)-L-2,3-diaminopropyl] -L-proline-t-butyl ester in Example 3. Following the removal of the tert-butoxycarbonyl and tert-butyl ester groups with trifluoroacetic acid, the tripeptide and 2-oxo-4-phenylbutyric acid were condensed in the presence of sodium cyanoborohydride in the manner described in Example 3. The reaction was followed by the removal of benzyloxycarbonyl group with 30-32% HBr in glacial acetic acid to afford N-[N²-(carboxy-3-phenylpropyl)-N³-β-alanyl-L-2,3-diaminopropyl]-L-proline. The nmr spectrum was consistent with structure.

EXAMPLE 7

N-[N²-(1-Carboxy-3-phenylpropyl)-N³-glycyl-D,L-2,3-diaminopropyl]-L-proline

N²-Tosyl-N³-benzyloxycarbonyl-D,L-2,3-diaminopropionic acid was prepared from N-benzyloxycarbonyl-D,L-2,3-diaminopropionic acid and p-toluene sulfonyl chloride by the method of B. C. Barrass (J. C. S., 3134, 1957). The product was coupled with L-proline benzyl ester using DCC. Following the removal of N³-benzyloxycarbonyl with 30-32% HBr/HOAc, the free amino was coupled in the established way to N-tert-butoxycarbonyl glycine using DCC. Treatment of N-[N²-tosyl-N³-(N-t-Boc-glycyl)-D,L-2,3-diaminopropyl]-L-proline benzyl ester with sodium and liquid ammonia removed the tosyl and benzyl ester protecting groups. The reductive alkylation of the resulting product with 2-oxo-4-phenylbutyric acid in the presence of sodium cyanoborohydride at pH=7 was carried out in the usual way. After Dowex 50 (H+) work up, the product was treated with trifluoroacetic acid for one hour at room temperature. TFA was stripped off and the product was then placed on Dowex 50 (H+) column followed by elution with 2% pyridine-H₂O to obtain N-[N²-(1-carboxy-3-phenylpropyl)-N³-glycyl-D,L-2,3-diaminopropyl]-L-proline. Further purification by LH-20 chromatograph to yielded pure product. The mass spectrum showed M+ =780 m/e (MW+5TMS) and 765 m/e, which was loss of methyl (15). Also, observed was 708 m/e (MW+4TMS), 693 m/e (−15(CH₃) from 708 m/e) and 591 m/e which corresponded to a loss of 117 (—CO₂TMS) from 700 m/e. The nmr was consistent with structure.

EXAMPLE 8

N-[N²-(1-Carboxy-3-phenylpropyl)-N³-methyl-N³-glycyl-D,L-2,3-diaminopropyl]-L-proline N³-Methyl-N³-benzyloxycarbonyl-D,L-2,3-diaminopropionic acid was prepared from N³-methyl-D,L-2,3-diaminopropionic acid and N-benzyloxycarbonyloxy-5-norbornene-2,3-dicarboximide in the manner described in Example 1. The N²-amino group was protected with tert-butoxycarbonyl using di-tert-butyl dicarbonate. The resulting N-protected amino acid was coupled with L-proline-tert-butylester using DCC. Following hydrogenation (10% Pd-C) with ammonium formate, the N³-methylamino group was coupled with N-benzyloxycarbonyl glycine to afford fully protected tripeptide, N-[N²-t-Boc-N³-methyl-N ³-(N-Cbz-glycyl)-D,L-2,3-diaminopropyl]-L-proline-t-butyl ester. Deprotection of the tert-butoxycarbonyl and tert-butyl ester groups using trifluoroacetic acid at room temperature afforded the TFA salt of N-[N³-methyl-N³-(N-Cbz-glycyl)-D,L-2,3-diaminopropyl]-L-proline. The reductive alkylation of the TFA salt with 2-oxo-4-phenylbutyric acid in the presence of sodium cyanoborohydride was carried out in the usual way. This reaction was followed by the removal of the benzyloxycarbonyl group with 30-32% HBr/HOAc to afford N-[N²-(1-carboxy-3-phenylpropyl)-N³-methyl-N³-glycyl-D,L-2,3-diaminopropyl]-L-proline. The mass spectrum (silylated) showed M+ 650; 635 m/e (M+—CH₃) and 436 m/e (M±CO proline TMS). The nmr spectrum in deuteromethanol showed aromatic singlet (5H) at 7.16 ppm; N-methyl (3H) at 3.0 ppm and proline multiplet at 2 ppm.

EXAMPLE 9

N-[N²-(1(S)-Carboxy-3-phenylpropyl)-N⁶-(2-methylalanyl)-L-lysyl]-L-proline

A solution of 406 mg (0.001 mole) of N-[N²-(1(S)-carboxy-3-phenylpropyl)-L-lysyl]-L-proline and 252 mg (0.003 mole) of sodium bicarbonate in 4 ml of water was treated with a solution of 334 mg (0.001 mole) of N-Cbz-α-aminoisobutyric acid N-hydroxysuccinimide ester in 2 ml of acetonitrile. The resulting solution was stirred at room temperature overnight and concentrated in vacuo to two-thirds of the original volume and acidified with 2.5 N HCl. The resulting insoluble gum (380 mg) was dissolved in 10 ml of methanol and hydrogenated over 10% Pd-C catalyst. After filtration and freeze-drying there was obtained 180 mg of N[N²-(1-(S)carboxy-3-phenylpropyl)-N⁴-(2-methylalanyl)-L-lysyl]-L-proline. The mass spectrum (FAB) showed 491 (M+ +1) and 513 (M+ +Na).

EXAMPLE 10

N-[N²-(1-Carboxy-3-phenylpropyl)-N⁴-(2-methylalanyl)-L-2,4-diamino-n-butyryl]-L-proline N-[N²-(1-carboxy-3-phenylpropyl)-N⁴-(N-Cbz-2-methylalanyl)-L-2,4-diamino-n-butyryl]-L-proline was prepared from N-[N²-(1-carboxy-3-phenylpropyl)-L-2,4-diaminobutyryl]-L-proline and N-Cbz-α-aminoisobutyric acid N-hydroxysuccinimide ester using the procedure described in Example 9. The N-benzyloxycarbonyl group was removed by hydrogenation to afford N-[N²-(1-carboxy-3-phenylpropyl)-N⁴-(2-methylalanyl)-L-2,4-diamino-n-butyryl]-L-proline as a white fluffy solid (yield-58%). The mass spectrum (FAB) showed M+463.

EXAMPLE 11

N-[N²-(1-(S)-Carboxy-3-phenylpropyl)-N⁶-(L-phenylalanyl)-L-lysyl]-L-proline

Using the procedure of Example 2, 210 mg of N-[N²-(1(S)-carboxy-3-phenylpropyl)-N⁶-(N-t-Boc-L-phenylalanyl)-L-lysyl-L-proline was prepared from 405 mg of N-[N²-(1(S)-carboxy-3-phenylpropyl)-L-lysyl]-L-proline and 363 mg (0.001 mole) of N-t-Boc-L-phenylalanyl N-hydroxy succinic ester. The t-Boc protecting group was removed by treatment with 5 ml of trifluoroacetic acid, and the product was chromatographed on Dowex 50 W-2X using 2% pyridine in water and then freeze dried. There was obtained 38.5 mg of N-[N²-(1(S)-carboxy-3-phenylpropyl)-N⁶-(L-phenylalanyl)-L-lysyl-L-proline as a fluffy white solid. The mass spectrum (FAB) showed the highest mass to be M+553.

EXAMPLE 12

N-[N2-(1-(S)-Carboxy-3-phenylpropyl)-N⁶-(L-prolyl)-L-lysyl-L-proline

The coupling of N-[N²-(1(S)-carboxy-3-phenylpropyl-L-lysyl]-L-proline (406 mg, 0.001 mole) and N-Cbz-L-proline N-hydroxysuccinimide ester (347 mg 0.001 mole) under the conditions described in Example 9 gave N-[N²-(1(S)-carboxy-3-phenylpropyl)-N⁶-(N-Cbz-L-prolyl)-L-lysyl-L-proline in quantitative yield. The N-Cbz group was removed by hydrogenation as described yielding 300 mg of N-[N²-(1(S)-carboxy-3-phenylpropyl)-N⁶-(L-prolyl)-L-lysyl]-L-proline. The mass spectrum (FAB) showed 503 (M+ +1).

EXAMPLE 13

N-[N²-(1(S)-Carboxy-3-phenylpropyl)-N⁶-sarcosyl-L-lysyl]-L-proline

By substituting 430 mg (0.001 mole) of N-t-Boc sarcosine N-hydroxy succinimide ester for the N-t-Boc glycine N-hydroxy succinimide ester in Example 9, N-[N²-(1(S)-carboxy-3-phenylpropyl)-N⁶-sarcosyl-L-lysyl]-L-proline was obtained in 72% yield. The mass spectrum (FAB) showed 477 (M+ +1).

EXAMPLE 14

N-[N²-(1(S)-Carboxy-3-phenylpropyl)-N⁴-glycyl-L-2,4-diamino-n-butyryl]-L-proline Following the procedure of Example 9 and using 377 mg (0.001 mol) of N-[N²-(1(S)-carboxy-3-phenylpropyl)-L-2,4-diamino n-butyryl]-L-proline and 306 mg (0.001 mole) of N-Cbz glycine N-hydroxy succinimide ester, there was obtained 290 mg of N-[N²-(1(S)-carboxy-3-phenylpropyl)-N⁴-glycyl-L-2,4-diamino-n-bytyryl]-L-proline. The mass spectrum (FAB) showed 435 (M+ +1) and 457 (M+ +Na).

EXAMPLE 15

N-[N²-(1(S)-Carboxy-3-phenylpropyl)-N⁴-β-alanyl-L-2,4-diamino-n-butyryl]-L-proline In the manner described in Example 2 and using 378 mg of N-[N²-(1(S)-carboxy-3-phenylpropyl)-L-2,4-diamino-n-butyryl)]-L-proline and 286 mg of N-t-Boc-]-β-alanine N-hydroxysuccinimide ester. There was obtained 206 mg of N-[N²-(1(S)-carboxy-3-phenylpropyl)-N⁴-β-alanyl-L-2,4-diamino-n-butyryl]-L-proline. The mass spectrum (FAB) showed 449 (M+ +1).

EXAMPLE 16

Compounds of Formula II:

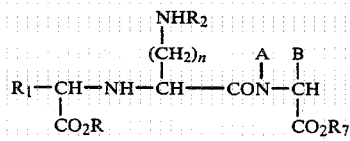

Compounds of formula II can be synthesized by coupling initially protected amino acids having the formulae:

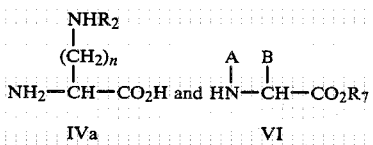

to obtain dipeptides having the formula:

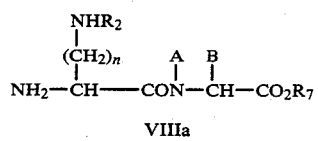

These dipeptides can, in turn, be reductively alkylated with keto acides or keto esters ($R_1COCO_2R$) to obtain formula II compounds. These methods can be preformed following the procedures described in Example 1 above. In the foregoing formulae, $R_2$, $R_7$, A, B and n are as defined hereinabove.

The amino acids and keto acids or keto esters required for these reactions are known except for those amino acids (IVa) wherein $R_2$ is methyl. Such amino acids can be synthesized by methylation of properly protected α,ω-diaminoacids using formaldehyde and NaCNBH₃. The protecting groups which can be typically employed include $N^\alpha$-t-butoxycarbonyl, $N^\omega$-monobenzyl, $C^1$-t-butyl, $N^\omega$-benzyloxycarbonyl groups, and the like.

The formula II compounds which can thus obtained are illustrated in Table I below:

TABLE I
Illustrative Compounds of Formula II

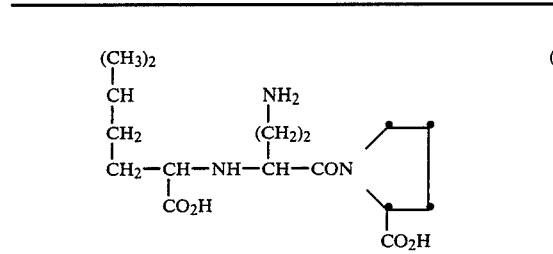 (a)

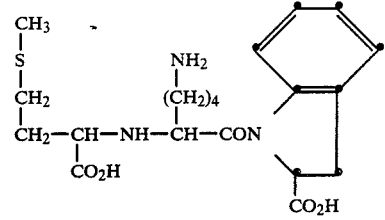 (b)

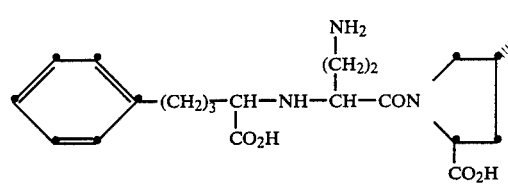 (c)

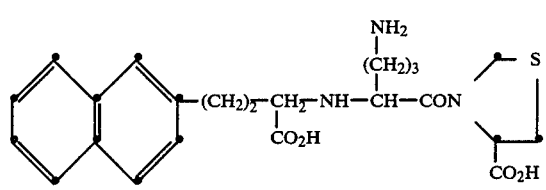 (d)

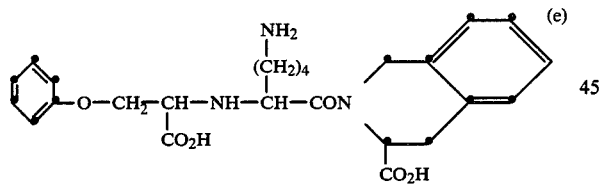 (e)

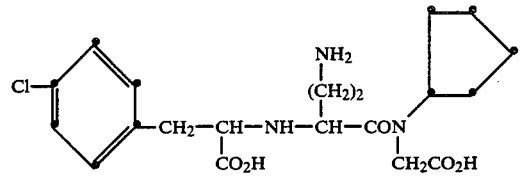 (f)

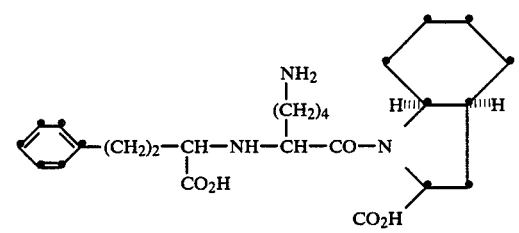 (g)

TABLE I-continued
Illustrative Compounds of Formula II

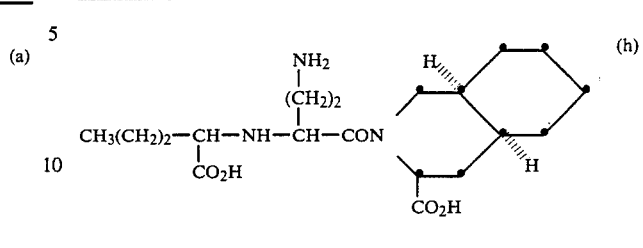 (h)

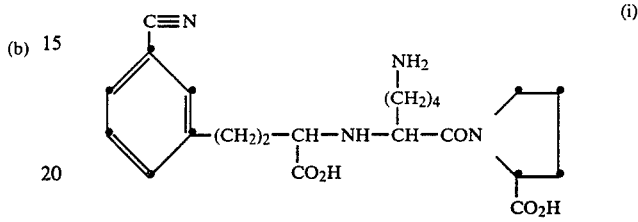 (i)

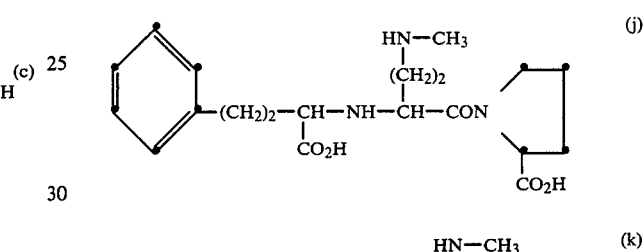 (j)

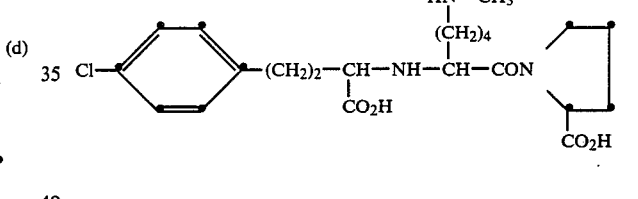 (k)

EXAMPLE 17
Compounds of Formula I

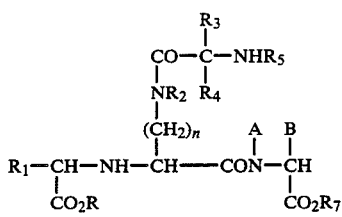

Compounds of formulala II can be coupled with N-protected carboxyl activated amino acids having the formula

 (III)

as described in Examples 2 and 4 above to obtain formula I compounds after removal of protecting groups.

Some examples of the formula I compounds which can be thus obtained are illustrated in Table II below:

TABLE II
Illustrative Compounds of Formula I
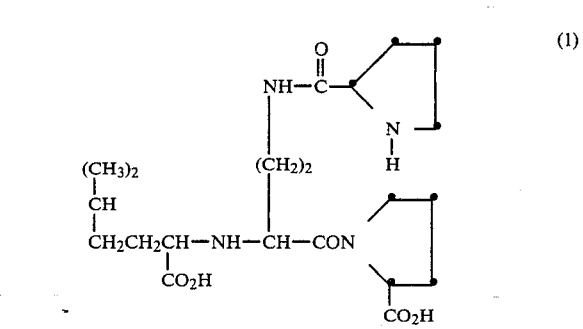 (l)
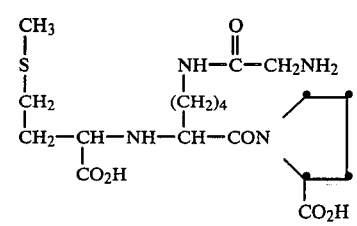 (m)
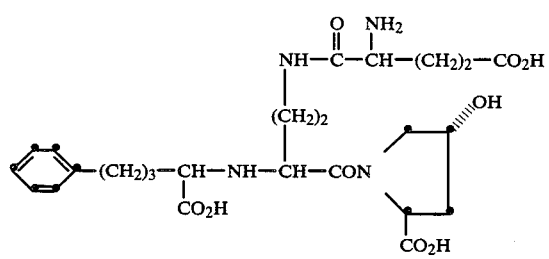 (n)
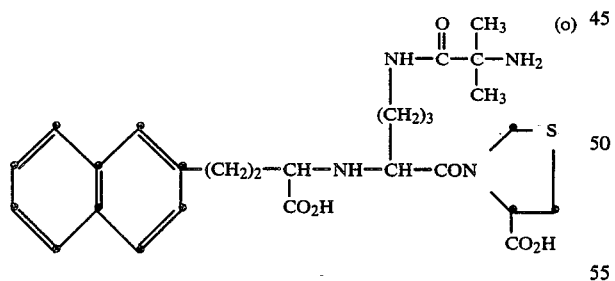 (o)
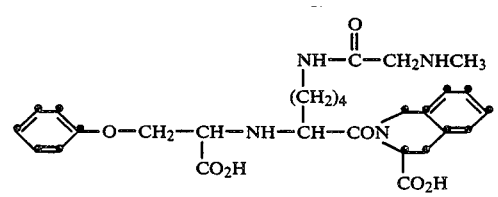 (p)
TABLE II-continued
Illustrative Compounds of Formula I
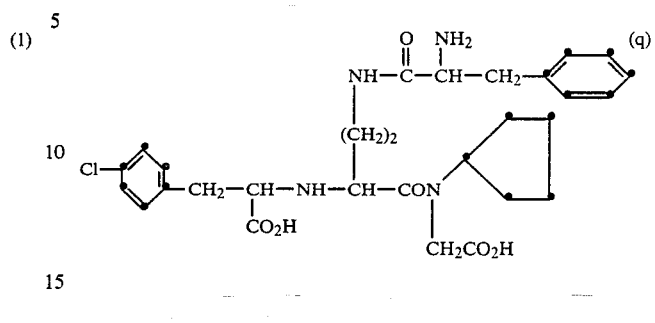 (q)
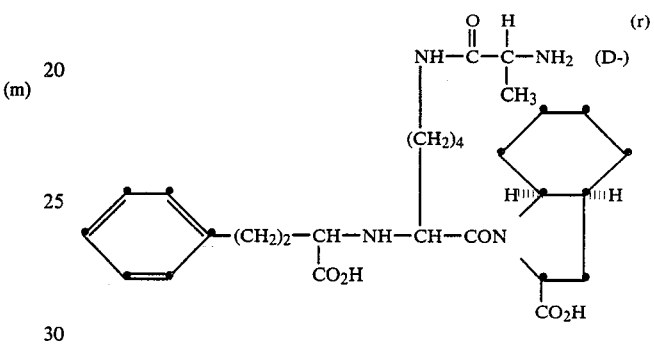 (r)
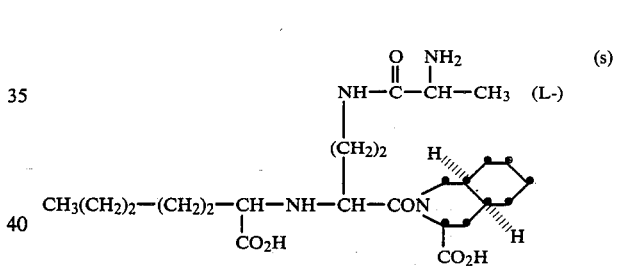 (s)
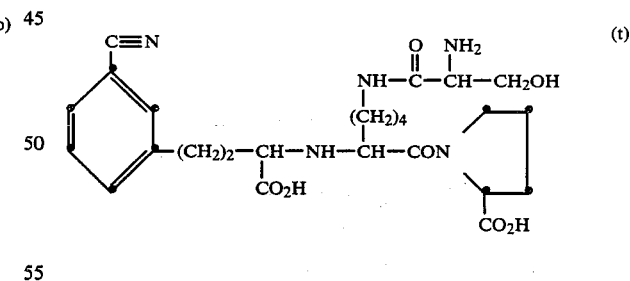 (t)
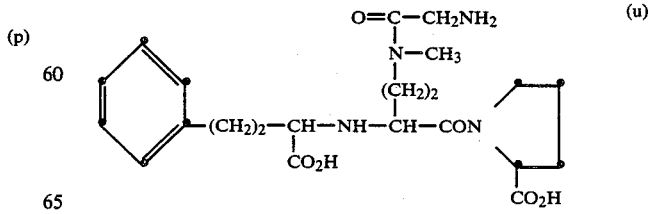 (u)

TABLE II-continued
Illustrative Compounds of Formula I

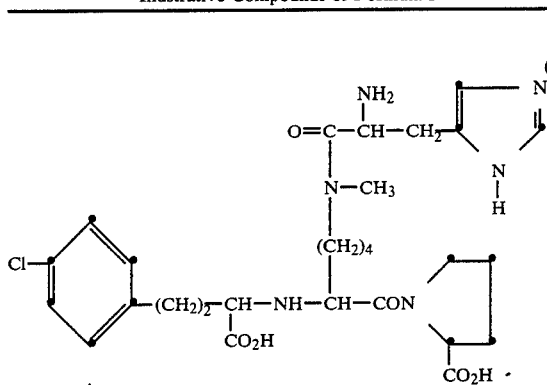
(v)

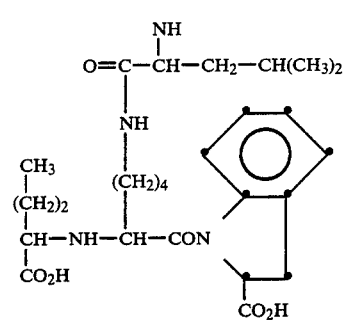
(w)

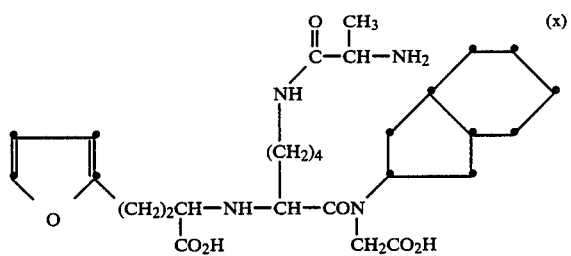
(x)

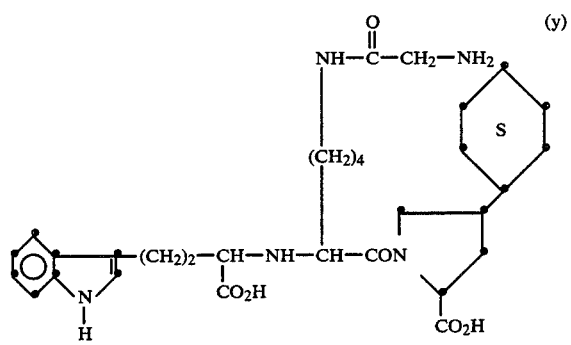
(y)

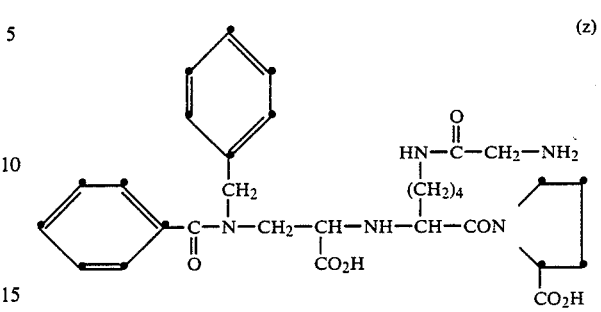
(z)

What is claimed is:
1. A compound of the formula:

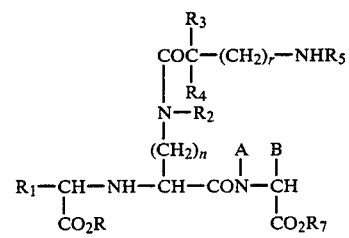
I wherein:

R and $R_7$ are independently hydrogen, loweralkyl, aryl, aralkyl;

$R^1$ is hydrogen; alkyl of from 1–12 carbon atoms which include branched and unsaturated groups and cyclic groups of 3–9 carbon atoms; substituted lower alkyl of 2–8 carbon atoms wherein the substituent(s) are halo, hydroxy, carboxy, carboxamido, loweralkylthio, loweralkoxy, loweralkoxycarbonyl, arylthio, aryloxy, aralkylthio, aralkyloxy, amino, loweralkylamino, diloweralkylamino, arylamino, arloweralkylamino, acylamino, acyl loweralkylamino, acyl arylamino, acyl aralkylamino, =O, =S or ureido; benzofused cycloalkyl and bicycloalkyl of 8 to 12 carbon atoms which can be substituted by one or more of the foregoing substituents; aryl, arloweralkyl, heteroaryl, heteroarloweralkyl, and those groups substituted by one or more of the foregoing substituents, the aryl or heteroaryl portions thereof being optionally mono-, di- or trisubstituted by halo, loweralkyl, hydroxy, loweralkoxy, amino, aminoloweralkyl, substituted aminoloweralkyl, hydroxyloweralkyl, acylamino, carboxy, halolower alkyl, nitro, cyano or sulfonamido; all of said foregoing substituents containing an aryl or heteroaryl group in which the aromatic rings are partially or completely hydrogenated;

n is 1 to 5;

r is 0 to 3;

$R_2$ is hydrogen, loweralkyl;

$R_3$ is hydrogen, aryl, hydroxyaryl, loweralkyl, loweralkyl substituted with aryl, carboxy, heteroaryl, amino, hydroxy, guanidino, alkylthio, mercapto, or alkyloxy;

$R_4$ and $R_5$ are independently hydrogen, loweralkyl; or, $R_3$ and $R_5$ can be joined to form a 5- to 6-membered ring having the formula:

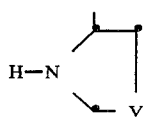

wherein V is —CH₂CH₂—, —CH₂—, S, —CH-(OR₂)— and wherein R₂ is the same as defined above;

A is loweralkyl, C₃-C₈ cycloalkyl; C₈-C₁₂ bicycloalkyl; benzofused C₃-C₈ cycloalkyl; perhydrobenzofused C₃-C₈ cycloalkyl; aryl; aralkyl; heteroaryl; heteroaralkyl; perhydroheteroaryl, or perhydroheteroaralkyl; all of which can be substituted by loweralkyl, loweralkoxy, halo, hydroxy, amino or acylamino;

B is hydrogen or loweralkyl; or, A and B can be joined, together with the N and C atoms to which they are attached to form a ring having the formulae

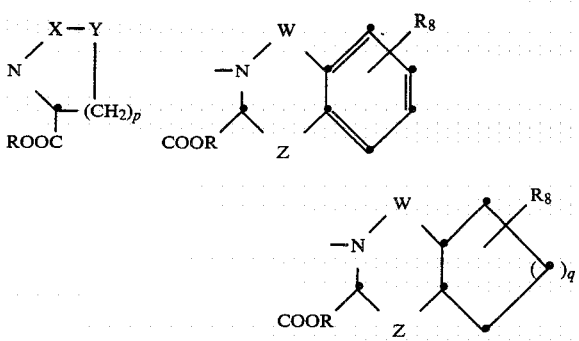

wherein:

X and Y taken together are —CH₂—CH₂—,

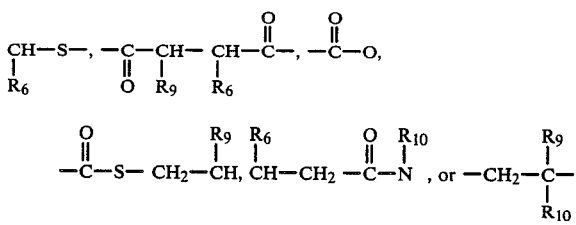

wherein R₆ is hydrogen or loweralkyl;

R₉ is hydrogen; lower alkyl; cycloalkyl; aryl; aralkyl; heteroaryl; heteroaralkyl; loweralkyloxy; loweralkylthio; aryloxy; arylthio; arloweralkyloxy; arloweralkylthio; acyloxy; amino; mono- or disubstituted loweralkylamino and arloweralkylamino; heteroarloweralkylamino; acylamino in which the acyl group can be loweralkanoyl, arloweralkanoyl, aroyl, heteroaroyl, heteroarloweralkanoyl; carbamoyloxy; or, N-substituted carbamoyloxy; the aromatic ring in said foregoing substituents being optionally mono-, di- or trisubstituted by loweralkyl, loweralkoxy, hydroxy, amino, loweralkylthio, halo, lowerhydroxyalkyl, loweraminoalkyl, sulfonamido, cyano, nitro, aryl, aryloxy, arylthio, or aralkyl; the aromatic rings in said groups containing aryl or heteroaryl groups being completely or partially hydrogenated;

R₁₀ is hydrogen; loweralkyl; aryl; substituted aryl; aralkyl; or, cycloalkyl; or R₉ and R₁₀ taken together can form a 5 or 6 membered ring which can contain 0, 1 or 2 S or O atoms;

p is 1 to 3;
q is 1 to 3;
W is absent; —CH₂, or

Z is —(CH₂)ₘ— wherein m is 0 to 2 provided that m is not 0 when W is absent;

R₈ is hydrogen; loweralkyl; loweralkoxy; hydroxy, halo; loweralkylthio; or, amino; and, the pharmaceutically acceptable salts thereof.

2. A compound of claim 1 which is: N-[N²-(1(S)-carboxy-3-phenylpropyl)-N⁶-glycyl-L-lysyl]-L-proline.

3. A compound of claim 1 which is: N-[N²-(1-carboxy-3-phenylpropyl)-N⁵-glycyl-L-ornithyl]-L-proline.

4. A compound of claim 1 which is: N-[N²-(1-carboxy-3-phenylpropyl)-N⁴-glycyl-L-2,4-diamino-n-butyryl]-L-proline.

5. A compound of claim 1 which is: N-[N²-(carboxy-3-phenylpropyl)-N³-L-alanyl-L-2,3-diaminopropyl]-L-proline.

6. A compound of claim 1 which is: N-[N²-(ethoxycarbonyl-3-phenylpropyl)-N⁵-glycyl-L-ornithyl]-L-proline.

7. A compound of claim 1 which is: N-[N²-(1-carboxy-3-phenylpropyl)-N³-β-alanyl-L-2,3-diaminopropyl]-L-proline.

8. A compound of claim 1 which is: N-[N²-(1-carboxy-3-phenylpropyl)-N³-glycyl-D,L-2,3-diaminopropyl]-L-proline.

9. A compound of claim 1 which is: N-[N²-(1-carboxy-3-phenylpropyl)-N³-methyl-N³-glycyl-D,L-2,3-diaminopropyl]-L-proline.

10. A compound of claim 1 which is: N-[N²-(1(S)-carboxy-3-phenylpropyl)-N⁶-(2-methylalanyl)-L-lysyl]-L-proline.

11. A compound of claim 1 which is: N-[N²-(1-carboxy-3-phenylpropyl)-N⁴-(2-methylalanyl)-L-2,4-diamino-n-butyryl]-L-proline.

12. A compound of claim 1 which is: N-[N²-(1(S)-carboxy-3-phenylpropyl)-N⁶-(L-phenylalanyl)-L-lysyl]-L-proline.

13. A compound of claim 1 which is: N-[N²-(1(S)-carboxy-3-phenylpropyl)-N⁶-(L-prolyl)-L-lysyl]-L-proline.

14. A compound of claim 1 which is: N-[N²-(1(S)-carboxy-3-phenylpropyl)-N⁶-sarcosyl-L-lysyl]-L-proline.

15. A compound of claim 1 which is: N-[N²-(1(S)-carboxy-3-phenylpropyl)-N⁴-glycyl-L-2,4-diamino-n-butyryl]-L-proline.

16. A composition useful in the treatment of hypertension which comprises a pharmaceutically acceptable carrier and an antihypertensively effective amount of a compound of the formula:

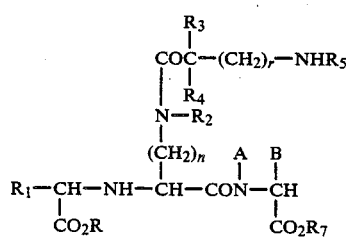

wherein:

R and $R_7$ are independently hydrogen, loweralkyl, aryl, aralkyl;

$R^1$ is hydrogen; alkyl of from 1-12 carbon atoms which include branched and unsaturated groups and cyclic groups of 3-9 carbon atoms; substituted lower alkyl of 2-8 carbon atoms wherein the substituent(s) are halo, hydroxy, carboxy, carboxamido, loweralkylthio, loweralkoxy, loweralkoxycarbonyl, arylthio, aryloxy, aralkylthio, aralkyloxy, amino, loweralkylamino, diloweralkylamino, arylamino, arloweralkylamino, acylamino, acyl loweralkylamino, acyl arylamino, acyl aralkylamino, =O, =S or ureido; benzofused cycloalkyl and bicycloalkyl of 8 to 12 carbon atoms which can be substituted by one or more of the foregoing substituents; aryl, arloweralkyl, heteroaryl, heteroarloweralkyl, and those groups substituted by one or more of the foregoing substituents, the aryl or heteroaryl portions thereof being optionally mono-, di- or trisubstituted by halo, loweralkyl, hydroxy, loweralkoxy, amino, aminoloweralkyl, substituted aminoloweralkyl, hydroxyloweralkyl, acylamino, carboxy, halolower alkyl, nitro, cyano or sulfonamido; all of said foregoing substituents containing an aryl or heteroaryl group in which the aromatic rings are partially or completely hydrogenated;

n is 1 to 5;

r is 0 to 3;

$R_2$ is hydrogen, loweralkyl;

$R_3$ is hydrogen, aryl, hydroxyaryl, loweralkyl, loweralkyl substituted with aryl, carboxy, heteroaryl, amino, hydroxy, guanidino, alkylthio, mercapto, or alkyloxy;

$R_4$ and $R_5$ are independently hydrogen, loweralkyl; or, $R_3$ and $R_5$ can be joined to form a 5- to 6-membered ring having the formula:

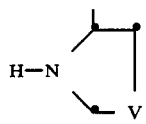

wherein V is —CH$_2$CH$_2$—, —CH$_2$—, S, —CH(OR$_2$)— and wherein $R_2$ is the same as defined above;

A is loweralkyl, C$_3$–C$_8$ cycloalkyl; C$_8$–C$_{12}$ bicycloalkyl; benzofused C$_3$–C$_8$ cycloalkyl; perhydrobenzofused C$_3$–C$_8$ cycloalkyl; aryl; aralkyl; heteroaryl; heteroaralkyl; perhydroheteroaryl, or perhydroheteroaralkyl; all of which can be substituted by loweralkyl, loweralkoxy, halo, hydroxy, amino or acylamino;

B is hydrogen or loweralkyl; or, A and B can be joined, together with the N and C atoms to which they are attached to form a ring having the formulae

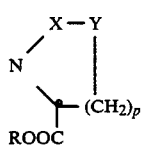 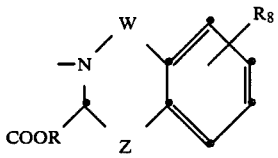

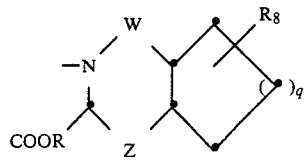

wherein:

X and Y taken together are —CH$_2$—CH$_2$—,

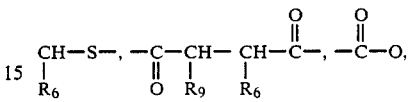

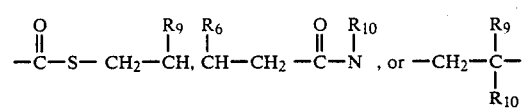

wherein $R_6$ is hydrogen or loweralkyl;

$R_9$ is hydrogen; lower alkyl; cycloalkyl; aryl; aralkyl; heteroaryl; heteroaralkyl; loweralkyloxy; loweralkylthio; aryloxy; arylthio; arloweralkyloxy; arloweralkylthio; acyloxy; amino; mono- or disubstituted loweralkylamino and arloweralkylamino; heteroarloweralkylamino; acylamino in which the acyl group can be loweralkanoyl, arloweralkanoyl, aroyl, heteroaroyl, heteroarloweralkanoyl; carbamoyloxy; or, N-substituted carbamoyloxy; the aromatic ring in said foregoing substituents being optionally mono-, di- or trisubstituted by loweralkyl, loweralkoxy, hydroxy, loweralkylthio, halo, lowerhydroxyalkyl, loweraminoalkyl, sulfonamido, cyano, nitro, aryl, aryloxy, arylthio, or aralkyl; the aromatic rings in said groups containing aryl or heteroaryl groups being completely or partially hydrogenated;

$R_{10}$ is hydrogen; loweralkyl; aryl; substituted aryl; aralkyl; or, cycloalkyl; or $R_9$ and $R_{10}$ taken together can form a 5 or 6 membered ring which can contain 0, 1 or 2 S or O atoms;

p is 1 to 3;

q is 1 to 3;

W is absent; —CH$_2$, or

Z is —(CH$_2$)$_m$— wherein m is 0 to 2 provided that m is not O when W is absent;

$R_8$ is hydrogen; loweralkyl; loweralkoxy; hydroxy, halo; loweralkylthio; or, amino; and, the pharmaceutically acceptable salts thereof.

17. The composition of claim 16 wherein said compound is a member of the group:

N-[N$^2$-(1(S)-carboxy-3-phenylpropyl)-N$^6$-glycyl-L-lysyl]-L-proline;

N-[N$^2$-(1-carboxy-3-phenylpropyl)-N$^5$-glycyl-L-ornithyl]-L-proline;

N-[N$^2$-(1-carboxy-3-phenylpropyl)-N$^4$-glycyl-L-2,4-diamino-n-butyryl]-L-proline;

N-[N$^2$-(carboxy-3-phenylpropyl)-N$^3$-L-alanyl-L-2,3-diaminopropyl]-L-proline;

N-[N$^2$-(ethoxycarbonyl-3-phenylpropyl)-N$^5$-glycyl-L-ornithyl]-L-proline;

N-[N²-(1-carboxy-3-phenylpropyl)-N³-β-alanyl-L-2,3-diaminopropyl]-L-proline;

N-[N²-(1-carboxy-3-phenylpropyl)-N³-glycyl-D,L-2,3-diaminopropyl]-L-proline;

N-[N²-(1-carboxy-3-phenylpropyl)-N³-methyl-N³-glycyl-D,L-2,3-diaminopropyl]-L-proline;

N-[N²-(1(S)-carboxy-3-phenylpropyl)-N⁶-(2-methylalanyl)-L-lysyl]-L-proline;

N-[N²-(1-carboxy-3-phenylpropyl)-N⁴-(2-methylalanyl)-L-2,4-diamino-n-butyryl]-L-proline;

N-[N²-(1(S)-carboxy-3-phenylpropyl)-N⁶-(L-phenylalanyl)-L-lysyl]-L-proline;

N-[N²-(1(S)-carboxy-3-phenylpropyl)-N⁶-(L-prolyl)-L-lysyl]-L-proline;

N-[N²-(1(S)-carboxy-3-phenylpropyl)-N⁶-sarcosyl-L-lysyl]-L-proline; and,

N-[N²-(1(S)-carboxy-3-phenylpropyl)-N⁴-glycyl-L-2,4-diamino-n-butyryl]-L-proline.

18. A composition useful in the treatment of hypertension which comprises a pharmaceutically acceptable carrier; an antihypertensively effective amount of a compound of the formula:

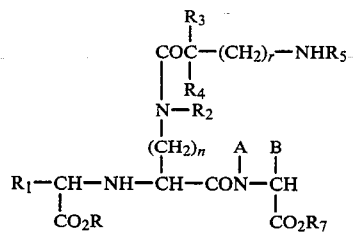

wherein:

R and $R_7$ are independently hydrogen, loweralkyl, aryl, aralkyl;

$R^1$ is hydrogen; alkyl of from 1-12 carbon atoms which include branched and unsaturated groups and cyclic groups of 3-9 carbon atoms; substituted lower alkyl of 2-8 carbon atoms wherein the substituent(s) are halo, hydroxy, carboxy, carboxamido, loweralkylthio, loweralkoxy, loweralkoxycarbonyl, arylthio, aryloxy, aralkylthio, aralkyloxy, amino, loweralkylamino, diloweralkylamino, arylamino, arloweralkylamino, acylamino, acyl loweralkylamino, acyl arylamino, acyl aralkylamino, =O, =S or ureido; benzofused cycloalkyl and bicycloalkyl of 8 to 12 carbon atoms which can be substituted by one or more of the foregoing substituents; aryl, arloweralkyl, heteroaryl, heteroarloweralkyl, and those groups substituted by one or more of the foregoing substituents, the aryl or heteroaryl portions thereof being optionally mono-, di- or trisubstituted by halo, loweralkyl, hydroxy, loweralkoxy, amino, aminoloweralkyl, substituted aminoloweralkyl, hydroxyloweralkyl, acylamino, carboxy, halolower alkyl, nitro, cyano or sulfonamido; all of said foregoing substituents containing an aryl or heteroaryl group in which the aromatic rings are partially or completely hydrogenated;

n is 1 to 5;

r is 0 to 3;

$R_2$ is hydrogen, loweralkyl;

$R_3$ is hydrogen, aryl, hydroxyaryl, loweralkyl, loweralkyl substituted with aryl, carboxy, heteroaryl, amino, hydroxy, guanidino, alkylthio, mercapto, or alkyloxy;

$R_4$ and $R_5$ are independently hydrogen, loweralkyl; or, $R_3$ and $R_5$ can be joined to form a 5- to 6-membered ring having the formula:

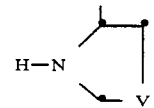

wherein V is —CH₂CH₂—, —CH₂—, S, —CH(OR₂)— and wherein $R_2$ is the same as defined above;

A is loweralkyl, $C_3$—$C_8$ cycloalkyl; $C_8$—$C_{12}$ bicycloalkyl; benzofused $C_3$—$C_8$ cycloalkyl; perhydrobenzofused $C_3$—$C_8$ cycloalkyl; aryl; aralkyl; heteroaryl; heteroaralkyl; perhydroheteroaryl, or perhydroheteroaralkyl; all of which can be substituted by loweralkyl, loweralkoxy, halo, hydroxy, amino or acylamino;

B is hydrogen or loweralkyl; or, A and B can be joined, together with the N and C atoms to which they are attached to form a ring having the formulae

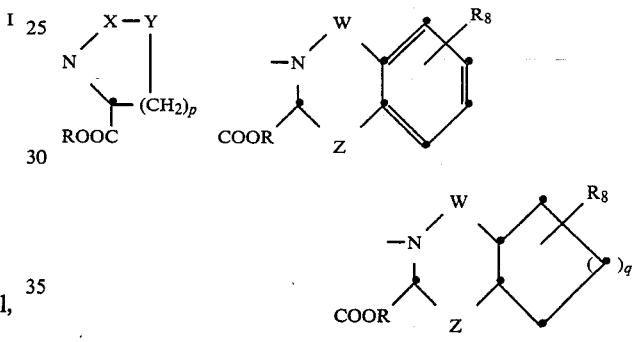

wherein:

X and Y taken together are —CH₂—CH₂—,

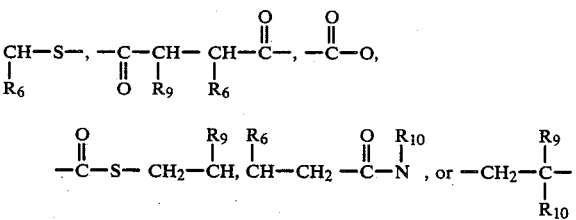

wherein $R_6$ is hydrogen or loweralkyl;

$R_9$ is hydrogen; lower alkyl; cycloalkyl; aryl; aralkyl; heteroaryl; heteroaralkyl; loweralkyloxy; loweralkylthio; aryloxy; arylthio; arloweralkyloxy; arloweralkylthio; acyloxy; amino; mono- or disubstituted loweralkylamino and arloweralkylamino; heteroarloweralkylamino; acylamino in which the acyl group can be loweralkanoyl, arloweralkanoyl, aroyl, heteroaroyl, heteroarloweralkanoyl; carbamoyloxy; or, N-substituted carbamoyloxy; the aromatic ring in said foregoing substituents being optionally mono-, di- or trisubstituted by loweralkyl, loweralkoxy, hydroxy, loweralkylthio, halo, lowerhydroxyalkyl, loweraminoalkyl, sulfonamido, cyano, nitro, aryl, aryloxy, arylthio, or aralkyl; the aromatic rings in said groups containing aryl or heteroaryl groups being completely or partially hydrogenated;

$R_{10}$ is hydrogen; loweralkyl; aryl; substituted aryl; aralkyl; or, cycloalkyl; or $R_9$ and $R_{10}$ taken together can form a 5 or 6 membered ring which can contain 0, 1 or 2 S or O atoms;

p is 1 to 3;
q is 1 to 3;
W is absent; —$CH_2$, or

Z is —$(CH_2)_m$—wherein m is 0 to 2 provided that m is not 0 when W is absent;

$R_8$ is hydrogen; loweralkyl; loweralkoxy; hydroxy, halo; loweralkylthio; or, amino; the pharmaceutically acceptable salts thereof; and, an antihypertensive and/or diuretic compound selected from the group consisting of amiloride, atenolol, bendroflumethiazide, chlorothalidone, chlorothiazide, clonidine, cryptenamine acetate and cryptenamine tannates, deserpidine, diazoxide, ethacrynic acid, furosemide, guanethidene sulfate, hydralazine hydrochloride, hydrochlorothiazide, hydroflumethiazide, metolazone, metroproloItartate, methyclothiazide, methyldopa, methyldopate hydrochloride, minoxidil, (S)-1-{[2-(3,4-dimethoxyphenyl)ethyl]amino}-3-{[4-(2-thienyl)-1H-imidazol-2-yl]phenoxy}-2-propanol, polythiazide, the pivalogloxyethyl ester of methyldopa, indacrinone and variable ratios of its enantiomers, nifedipine, verapamil, dilthiazam, flumethiazide, bendroflumethiazide, atenolol, (+)-4-{3-{-[2-(1-hydroxycyclohexyl)ethyl]-4-oxo-2-thiazolidinyl}propyl}benzoic acid, bumethanide, prazosin, propranolol, rauwolfia serpentina, rescinnamine, reserpine, spironolactone, timolol, trichlormethiazide, benzthiazide, quinethazone, tricrynafan, triamterene, acetazolamide, aminophylline, cyclothiazide, merethoxylline procaine, and the like, as well as admixtures and combinations thereof.

19. The composition of claim 18 wherein said antihypertensively effective compound is a member of the group:

N-[$N^2$-(1(S)-carboxy-3-phenylpropyl)-$N^6$-glycyl-L-lysyl]-L-proline;
N-[$N^2$-(1-carboxy-3-phenylpropyl)-$N^5$-glycyl-L-ornithyl]-L-proline;
N-[$N^2$-(1-carboxy-3-phenylpropyl)-$N^4$-glycyl-L-2,4-diamino-n-butyryl]-L-proline;
N-[$N^2$-(carboxy-3-phenylpropyl)-$N^3$-L-alanyl-L-2,3-diaminopropyl]-L-proline;
N-[$N^2$-(ethoxycarbonyl-3-phenylpropyl)-$N^5$-glycyl-L-ornithyl]-L-proline;
N-[$N^2$-(1-carboxy-3-phenylpropyl)-$N^3$-β-alanyl-L-2,3-diaminopropyl]-L-proline;
N-[$N^2$-(1-carboxy-3-phenylpropyl)-$N^3$-glycyl-D,L-2,3-diaminopropyl]-L-proline;
N-[$N^2$-(1-carboxy-3-phenylpropyl)-$N^3$-methyl-$N^3$-glycyl-D,L-2,3-diaminopropyl]-L-proline;
N-[$N^2$-(1(S)-carboxy-3-phenylpropyl)-$N^6$-(2-methylalanyl)-L-lysyl]-L-proline;
N-[$N^2$-(1-carboxy-3-phenylpropyl)-$N^4$-(2-methylalanyl)-L-2,4-diamino-n-butyryl]-L-proline;
N-[$N^2$-(1(S)-carboxy-3-phenylpropyl)-$N^6$-(L-phenylalanyl)-L-lysyl]-L-proline;
N-[$N^2$-(1(S)-carboxy-3-phenylpropyl)-$N^6$-(L-prolyl)-L-lysyl-L-proline;
N-[$N^2$-(1(S)-carboxy-3-phenylpropyl)-$N^6$-sarcosyl-L-lysyl]-L-proline; and,
N-[$N^2$-(1(S)-carboxy-3-phenylpropyl)-$N^4$-glycyl-L-2,4-diamino-n-butyryl]-L-proline.

20. A method of treating hypertension which comprises administering to a patient in need of such treatment an antihypertensively effective amount of a compound of the formula:

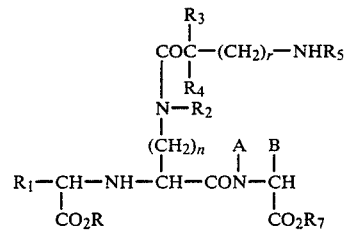

wherein:

R and $R_7$ are independently hydrogen, loweralkyl, aryl, aralkyl;

$R^1$ is hydrogen; alkyl of from 1–12 carbon atoms which include branched and unsaturated groups and cyclic groups of 3–9 carbon atoms; substituted lower alkyl of 2–8 carbon atoms wherein the substituent(s) are halo, hydroxy, carboxy, carboxamido, loweralkylthio, loweralkoxy, loweralkoxycarbonyl, arylthio, aryloxy, aralkylthio, aralkyloxy, amino, loweralkylamino, diloweralkylamino, arylamino, arloweralkylamino, acylamino, acyl loweralkylamino, acyl arylamino, acyl aralkylamino, =O, =S or ureido; benzofused cycloalkyl and bicycloalkyl of 8 to 12 carbon atoms which can be substituted by one or more of the foregoing substituents; aryl, arloweralkyl, heteroaryl, heteroarloweralkyl, and those groups substituted by one or more of the foregoing substituents, the aryl or heteroaryl portions thereof being optionally mono-, di- or trisubstituted by halo, loweralkyl, hydroxy, loweralkoxy, amino, aminoloweralkyl, substituted aminoloweralkyl, hydroxyloweralkyl, acylamino, carboxy, halolower alkyl, nitro, cyano or sulfonamido; all of said foregoing substituents containing an aryl or heteroaryl group in which the aromatic rings are partially or completely hydrogenated;

n is 1 to 5;
r is 0 to 3;
$R_2$ is hydrogen, loweralkyl;
$R_3$ is hydrogen, aryl, hydroxyaryl, loweralkyl, loweralkyl substituted with aryl, carboxy, heteroaryl, amino, hydroxy, guanidino, alkylthio, mercapto, or alkyloxy;
$R_4$ and $R_5$ are independently hydrogen, loweralkyl; or,
$R_3$ and $R_5$ can be joined to form a 5- to 6-membered ring having the formula:

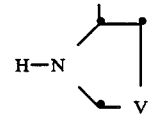

wherein V is —$CH_2CH_2$—, —$CH_2$—, S, —CH($OR_2$)— and wherein $R_2$ is the same as defined above;
A is loweralkyl, $C_3$–$C_8$ cycloalkyl;
$C_8$–$C_{12}$ benzofused
$C_3$–$C_8$ cycloalkyl; perhydrobenzofused $C_3$–$C_8$ cycloalkyl; aryl; aralkyl; heteroaryl; heteroaralkyl; perhydroheteroaryl, or perhydroheteroaralkyl; all of which can be substituted by loweralkyl, loweralkoxy, halo, hydroxy, amino or acylamino;

B is hydrogen or loweralkyl; or, A and B can be joined, together with the N and C atoms to which they are attached to form a ring having the formulae

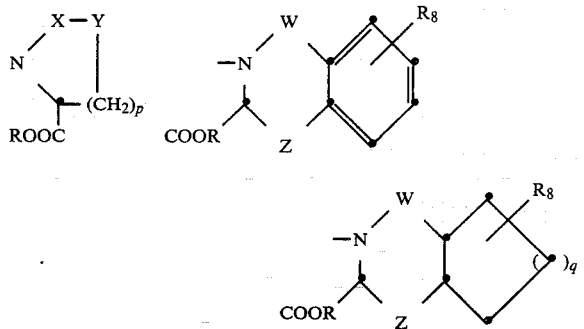

wherein:

X and Y taken together are —$CH_2$—$CH_2$—,

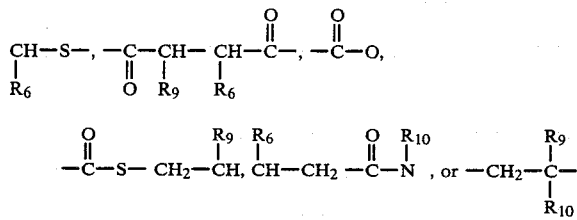

wherein $R_6$ is hydrogen or loweralkyl;

$R_9$ is hydrogen; lower alkyl; cycloalkyl; aryl; aralkyl; heteroaryl; heteroaralkyl; loweralkyloxy; loweralkylthio; aryloxy; arylthio; arloweralkyloxy; arloweralkylthio; acyloxy; amino; mono- or disubstituted loweralkylamino and arloweralkylamino; heteroarloweralkylamino; acylamino in which the acyl group can be loweralkanoyl, arloweralkanoyl, aroyl, heteroaroyl, heteroarloweralkanoyl; carbamoyloxy; or, N-substituted carbamoyloxy; the aromatic ring in said foregoing substituents being optionally mono-, di- or trisubstituted by loweralkyl, loweralkoxy, hydroxy, loweralkylthio, halo, lowerhydroxyalkyl, loweraminoalkyl, sulfonamido, cyano, nitro, aryl, aryloxy, arylthio, or aralkyl; the aromatic rings in said groups containing aryl or heteroaryl groups being completely or partially hydrogenated;

$R_{10}$ is hydrogen; loweralkyl; aryl; substituted aryl; aralkyl; or, cycloalkyl; or $R_9$ and $R_{10}$ taken together can form a 5 or 6 membered ring which can contain 0, 1 or 2 S or O atoms;

p is 1 to 3;

q is 1 to 3;

W is absent; —$CH_2$, or

Z is —$(CH_2)_m$— wherein m is 0 to 2 provided that m is not 0 when W is absent;

$R_8$ is hydrogen; loweralkyl; loweralkoxy; hydroxy, halo; loweralkylthio; or, amino; and, the pharmaceutically acceptable salts thereof.

21. The method of claim 20 wherein said compound is a member of the group:

N-[$N^2$-(1(S)-carboxy-3-phenylpropyl)-$N^6$-glycyl-L-lysyl]-L-proline;

N-[$N^2$-(1-carboxy-3-phenylpropyl)-$N^5$-glycyl-L-ornithyl]-L-proline;

N-[$N^2$-(1-carboxy-3-phenylpropyl)-$N^4$-glycyl-L-2,4-diamino-n-butyryl]-L-proline;

N-[$N^2$-(carboxy-3-phenylpropyl)-$N^3$-L-alanyl-L-2,3-diaminopropyl]-L-proline;

N-[$N^2$-(ethoxycarbonyl-3-phenylpropyl)-$N^5$-glycyl-L-ornithyl]-L-proline;

N-[$N^2$-(1-carboxy-3-phenylpropyl)-$N^3$-$\beta$-alanyl-L-2,3-diaminopropyl]-L-proline;

N-[$N^2$-(1-carboxy-3-phenylpropyl)-$N^3$-glycyl-D,L-2,3-diaminopropyl]-L-proline;

N-[$N^2$-(1-carboxy-3-phenylpropyl)-$N^3$-methyl-$N^3$-glycyl-D,L-2,3-diaminopropyl]-L-proline;

N-[$N^2$-(1(S)-carboxy-3-phenylpropyl)-$N^6$-(2-methylalanyl)-L-lysyl]-L-proline;

N-[$N^2$-(1-carboxy-3-phenylpropyl)-$N^4$-(2-methylalanyl)-L-2,4-diamino-n-butyryl]-L-proline;

N-[$N^2$-(1(S)-carboxy-3-phenylpropyl)-$N^6$-(L-phenylalanyl)-L-lysyl]-L-proline;

N-[$N^2$-(1(S)-carboxy-3-phenylpropyl)-$N^6$-(L-prolyl)-L-lysyl-L-proline;

N-[$N^2$-(1(S)-carboxy-3-phenylpropyl)-$N^6$-sarcosyl-L-lysyl]-L-proline; and,

N-[$N^2$-(1(S)-carboxy-3-phenylpropyl)-$N^4$-glycyl-L-2,4-diamino-n-butyryl]-L-proline.

* * * * *